United States Patent [19]

Casagrande et al.

[11] Patent Number: 4,988,735
[45] Date of Patent: Jan. 29, 1991

[54] ETHYLENE DIAMINE ACTIVE CARDIOVASCULAR THERAPY

[75] Inventors: Cesare Casagrande, Arese; Francesco Santangelo; Maria L. Calabi, both of Milan, all of Italy

[73] Assignee: Simes, Vicenza, Italy

[21] Appl. No.: 197,977

[22] Filed: May 24, 1988

[30] Foreign Application Priority Data

Jun. 5, 1987 [IT] Italy ............................... 20800 A/87

[51] Int. Cl.$^5$ .................. A61K 31/165; C07C 217/58
[52] U.S. Cl. ..................................... 514/648; 514/554; 564/316
[58] Field of Search ..................... 564/316; 260/54.18; 514/558, 553, 554, 648

[56] References Cited

U.S. PATENT DOCUMENTS

| 3,321,523 | 5/1967 | Zellner | 564/370 |
| 3,400,155 | 5/1968 | Ehrhart et al. | 564/370 |
| 3,876,702 | 4/1975 | Petersen et al. | 564/316 |
| 4,381,305 | 4/1983 | Casagrande et al. | 564/316 X |
| 4,638,003 | 1/1987 | Chiarino et al. | 564/316 X |
| 4,723,039 | 2/1988 | Seitz et al. | 564/342 X |

FOREIGN PATENT DOCUMENTS 2279383 2/1976 France ................. 564/316

Primary Examiner—Richard L. Raymond
Attorney, Agent, or Firm—Stevens, Davis, Miller & Mosher

[57] ABSTRACT

The compound N,N'-dimethyl-N-(3,4,5-trimethoxybenzyl)-N'-[3,3-di-(4-fluorophenyl)-propyl]-ethylenediamine and its salts are described.

This compound is useful in the treatment of several cardiovascular pathologies.

5 Claims, No Drawings

ETHYLENE DIAMINE ACTIVE CARDIOVASCULAR THERAPY

The present invention relates to a compound useful in the cardiovascular therapy and, more particularly, it relates to the compound N,N'-dimethyl-N-(3,4,5-trimethoxybenzyl)-N'-[3,3-di-(4-fluorophenyl)-propyl]-ethylenediamine and to its use in the cardiovascular therapy.

In the European Patent No. 41,757 in the name of the same Applicant, compounds endowed with anti-spasmodic activity on vascular smooth muscle and with anti-allergic activity have been described, having general formula:

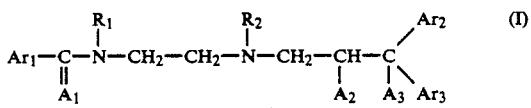

wherein
$R_1$ represents a hydrogen atom, a lower alkyl or arylalkyl;
$R_2$ represents a lower alkyl;
$Ar_1$ represents an optionally substituted aryl, arylalkyl or heterocycle;
$Ar_2$ and $Ar_3$, the same or different, represent an optionally substituted aryl;
$A_1$ represents an oxygen atom or two hydrogen atoms;
$A_2$ represents a hydrogen atom;
$A_3$ represents a hydrogen atom or hydroxy or, together with $A_2$, it represents a bond of double bond.

We have now found that one of the compounds comprised in general formula I, but which was not exemplified in the above European Patent, has unexpected pharmacological properties which make it particularly useful in the cardiovascular therapy.

Object of the present invention is, therefore, the compound N,N'-dimethyl-N-(3,4,5-trimethoxybenzyl)-N'-[3,3-di-(4-fluorophenyl)-propyl]-ethylenediamine of formula

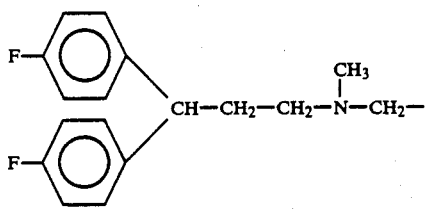

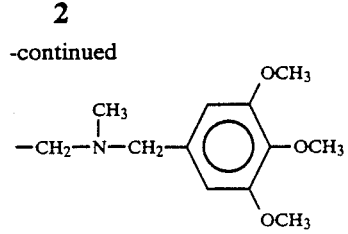

or its salts with pharmaceutically acceptable acids.

The compound of formula II not only has the same anti-spasmodic properties on smooth muscle than the compounds of formula I, with consequent favourable effects in decreasing vascular resistances and in increasing blood flow in different areas, but in addition it has, unexpectedly, the property of increasing the cardiac output and, at the same time, it does not induce an increase in heart rate. For these properties the compound of formula II is particularly suitable in the treatment of cardiac decompensation. A second unexpected property of compound II consists in its ability to specifically antagonize the effects of serotonin on blood platelets as well as on vessels and consequently compound II is useful in the therapy of coronary diseases and in other pathological conditions in which serotonin causes blood platelet aggregation and vasoconstriction.

This property is not shared by the tested compounds of formula I. Compound II, furthermore, resulted to be able to prevent the formation of arteriosclerotic plaques and therefore it is useful in the treatment of arteriosclerosis in a late stage as well as the early stage.

Also this property is not shared by the tested compounds of formula I.

Therefore, a further object of the present invention are pharmaceutical compositions containing compound II and useful in the treatment of cardiac decompensation, in the treatment of coronary diseases or in the preventive and curative treatment of arteriosclerosis.

It is worth noting that these pathological conditions appear sometimes contemporaneously in that they often have origins in mutual relation.

The preparation of compound II can be conveniently carried out according to the methods described in European Patent No. 41,757 for the synthesis of the compounds of formula I.

We have now found and it is a further object of the present invention, a new synthetic process which is particularly useful in the preparation of compound II.

This process consists in the reduction of a compound of formula

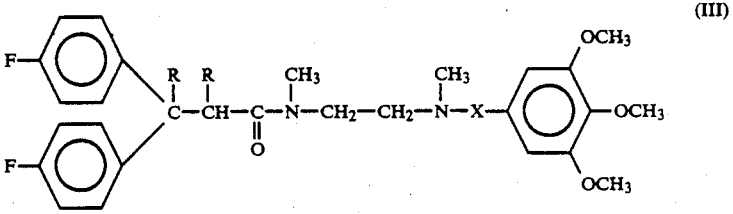

wherein both substituents R represent hydrogen atoms or together they form a second bond between the carbon atoms to which they are bonded; X represents a $CH_2$ or a

group.

The reduction of the compounds of formula III is carried out by means of known reducing agents able to reduce amidic carbonyl group and contemporaneously also the optional insaturation (when both substituents R form a second bond).

Suitable reducing agents are diborane and its complexes with ethers such as tetrahydrofuran, organic sulfides such as dimethylsulfide or amines such as morpholine.

When both substituents R are hydrogen atoms the reduction can be carried out also with metal hydrides such as lithiumaluminumhydride or aluminumhydride.

The reaction is carried out in an inert solvent, preferably in an ether solvent such as diethyl ether, tetrahydrofuran and dimethoxyethane, at a temperature between 0° C. and the boiling temperature of the reaction mixture.

The compounds of formula III are prepared by means of two consecutive acylation reactions of N,N-dimethylethylenediamine.

The acylations are carried out using a suitable reactive derivative of a carboxylic acid, preferably an acyl chloride, in an inert solvent such as ethyl acetate or methylene chloride, in the presence of a base such as an alkaline bicarbonate or a tertiary amine, for example triethylamine or pyridine, which may also act as solvent, or N-dimethylamino-pyridine.

It is preferred but it is not essential that during the first acylation reaction N,N'-dimethyl-ethylenediamine be protected at one of the nitrogens as for example, N,N'-dimethyl-N-benzylethylenediamine.

Before carrying out the second acylation, the protective group is removed by usual techniques, for example, by catalytic hydrogenation.

The reaction between N,N'-dimethyl-ethylenediamine and 3,3-di-(4fluorophenyl)-propionyl chloride or 3,3-di-(4-fluorophenyl)-2-propenoyl chloride gives the intermediates of formula

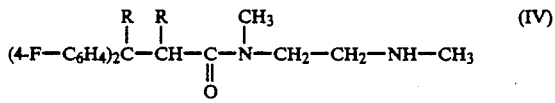

which, by reaction with 3,4,5-trimethoxybenzoyl chloride give the compounds of formula III wherein X is a carbonyl.

In a similar way, the reaction between N,N'-dimethyl-ethylenediamine and 3,4,5-trimethoxybenzoyl chloride gives the intermediate of formual

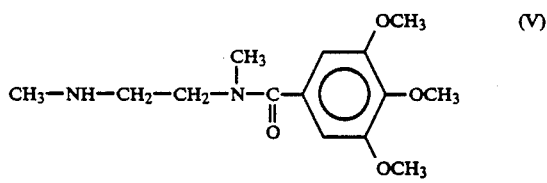

which is transformed into the compounds of formula III by reaction with 3,3-di-(4-fluorophenyl)-propionyl chloride or with 3,3-di-(4-fluorophenyl)-2-propenoyl chloride.

These acyl chlorides are known compounds described in J. Am. Chem. Sc., 70, 1612, (1948).

The preparation of the compounds of formula III wherein X=CH$_2$ can be carried out through a reductive alkylation of N,N'-dimethylethylenediamine or of an amine of formula IV, which is reacted with 3,4,5-trimethoxy-benzaldehyde and then reduced with sodium borohydride, sodium cyanoborohydride or by catalytic hydrogenation.

Alternatively, the compound of formula III wherein X=CH$_2$ can be obtained by reduction of the amidic carbonyl group of compound V before or after deprotection of the amino nitrogen.

The reaction product is acylated, then, according to what above described.

An alternative method for the above reaction for the preparation of the compounds of formula III wherein X=CH$_2$ consists in carrying out a condensation between 3,4,5-trimethoxy-benzaldehyde and N-methylethanolamine in the same above described reductive alkylation conditions.

The reaction product, N-methyl-N-(3,4,5-trimethoxybenzyl)-ethanolamine, is then converted to N,N'-dimethyl-N-(3,4,5-trimethoxybenzyl)-ethylenediamine by reaction with thionyl chloride and then with methylamine.

The so obtained product is then acylated according to the above described methods.

As above mentioned, compound II shows interesting pharmacological properties that make it particularly useful in the treatment of different diseases of the cardiovascular system and, for some aspects, also in the preventive treatment.

In hemodynamic tests on anesthetized dogs, compound II showed to induce a decrease in systemic and coronary vascular resistances like the best compounds described in European Patent No. 41,757.

Furthermore it also showed to induce an increase in cardiac output, so differing from the other tested compounds of formula I, without a contemporaneous increase in heart rate (see example 10). These properties make compound II particularly useful in the treatment of cardiac decompensation, both if caused by a coronary disease and if caused by another etiological origin, in that for such a use it is necessary that the drug, able to decrease vasoconstriction, does not depress cardiac functionality and does not increase heart rate.

Furthermore compound II showed to be able to antagonize, in a specific way, the effect of serotonin on blood platelets as well as on vessels (see example 11).

It is known that the release of serotonin from blood platelets during the aggregation is a mechanism of enhancement of the aggregation, of induction of direct vessel spasms, of strengthening of the spasms induced by other mediators. This mechanism is particularly active in vessels with endothelial damages and with arteriosclerotic plaques. The specific inhibition of serotonin represents a further utility aspect of compound II in cardiovascular therapy and particularly in coronary diseases.

Furthermore compound II resulted to be able to prevent the formation of arteriosclerotic plaques in rabbits on ipercholesterolemic diet and to inhibit arterial smooth muscle cell proliferation (see example 12).

Doses of 1 and 3 mg/kg s.c. twice a day reduced of 40 and 60% respectively the area of plaques present in aorta after 60 days of treatment.

The antagonism towards the formation of arteriosclerotic plaques is therapeutically useful not only in a condition of arteriosclerosis in a late stage, where there are vasospasmodic and anginal symptoms, but also in the early stage of the disease, before symptoms appear.

For its practical use in therapy compound II can be used as such or as a salt with a pharmaceutically acceptable acid.

The preparation of the salts is carried out according to known methods. Suitable pharmaceutically acceptable acids include hydrochloric, maleic, tartaric, sulphuric and phosphoric acid.

The present invention also relates to pharmeceutical compositions suitable for the administration of the compound of formula II or of its salts.

These compositions, which are prepared according to conventional techniques, contain a therapeutically useful amount of compound II together with a suitable carrier consisting in excipients for pharmaceutical use (solid, semi-solid or liquid) which depend on the selected administration route (oral, parenteral, rectal, transmucosal, transdermal or inhalatory).

The pharmaceutical compositions can be, then, solid (capsules, tablets, powders, coated tablets), liquid (solutions, suspensions or emulsions), semi-solid (suppositories, ointments, creams) and freeze-dried to be diluted before use.

Further excipients can also be included in the compositions such as pharmaceutically acceptable preserving agents, stabilizing agents, emulsifying agents, wetting agents, lubricants, salts to regulate osmotic pressure, buffers, colouring agents and flavouring agents.

The compositions can also be prepared, according to conventional techniques, so that they release the active ingredient slowly and in a controlled way.

This embodiment includes also medicated plasters useful for transdermal administration.

If desired, it is possible to add to the compositions other therapeutically useful substances which are compatible with compound II and have a complementary action to it.

The amount of compound II to be administered varies depeding on different factors among which the kind of disease to be treated, the general state of the patient, the individual response, the selected administration route can be mentioned.

In general, the dose for oral administration to be repeated 1-3 times a day will be beteen 5 and 200 mg of compound II or equivalent amounts of its salts.

For parenteral administration by intravenous route (single dose or perfusion) or by intramuscular route, 2 to 10 mg of compound II or equivalent amounts of its salts will be administered.

In order to better illustrate the present invention the following examples are now given.

PREPARATIVE EXAMPLES

EXAMPLE 1

Preparation of
N,N'-dimethyl-N-benzyl-N'-(3,4,5-trimethoxybenzyol)-ethylenediamine To a solution of N,N'-dimethhyl-N-benzyl-ethylenediamine (300 g) in pyridine (500 ml), 3,4,5-trimethoxybenzyol chloride (338 g) was added at portions.

After 1 hour at room temperature, water (200 ml) was added and the reaction mixture was evaporated under reduced pressure. The residue was dissolved in $CH_2Cl_2$ and washed with diluted NaOH.

The organic phase, dried on $Na_2SO_4$, was evaporated to dryness giving N,N'-dimethyl-N-benzyl-N'-(3,4,5-trimethoxybenzoyl)-ethylenediamine as a chromatographically pure oil (thin layer chromatography on silica gel, eluent: $CH_2Cl_2:CH_3OH:NH_4OH=86:10:0.6$, detection: U.V. light or $I_2$ vapours).

EXAMPLE 2

Preparation of
N,N'-dimethyl-N-(3,4,5-trimethoxybenzoyl)-ethylenediamine hydrochloride To a solution of N,N'-dimethyl-N-benzyl-N'-(3,4,5-trimethoxybenzoyl)-ethylenediamine (600 g), obtained as described in example 1, in ethanol 95% (2 l), acidified to pH 3 with concentrated HCl, Pd on carbon at 10% (120 g) was added.

The reaction mixture was hydrogenated at 50° C., under 10 atmospheres $H_2$ pressure.

After the theoric absorption of hydrogen, the catalyst was filtered off and the solution was evaporated under reduced pressure, the residue was crystallized from ethyl acetate obtaining N,N'-dimethyl-N-(3,4,5-trimethoxybenzoyl)-ethylenediamine hydrochloride (m.p. =137°-140° C.).

EXAMPLE 3

Preparation of
N,N'-dimethyl-N-benzyl-N'-(3,4,5-trimethoxybenzyl)-ethylenediamine A solution of N,N'-dimethyl-N-benzyl-N'-(3,4,5-trimethoxybenzoyl)-ethylenediamine (580 g), obtained as described in example 1, in THF (2.4 l) was added, under nitrogen, to a suspension of $LiAlH_4$ (60 g) in THF (120 ml).

After 1 hour at room temperature the excess of hydride was decomposed by adding carefully wet THF. The salts were filtered off and the solution was evaporated to dryness. The residue was dissolved in $CH_2Cl_2$, washed with diluted NaOH; the organic layer was dried on $Na_2SO_4$ and evaporated to dryness.

The residue was distilled giving N,N'-dimethyl-N-benzyl-N'-(3,4,5-trimethoxybenyl)-ethylenediamine (b.p. 150° C./0.5 mmHg) as a chromatographically pure oil (thin layer chromatography on silica gel, eluent: $CH_2Cl_2:CH_3OH:NH_4OH =86:10:0.6$, detection: U.V. light or $I_2$ vapours).

$^1$H-NMR (60 MHz, $CDCl_3$, TMS)

delta (ppm): 2.2 (3H, s); 2.4(3H, s); 2.6 (4H, m); 3.6 (2H, s); 4.0 (9H, s); 7.5 (7H, m).

The corresponding dihydrochloride was prepared by dissolution of the base in absolute ethanol and acidification with ethanol saturated by HCl (m.p. =245°-247° C.).

EXAMPLE 4

Preparation of
N-methyl-N-(3,4,5-trimethoxybenzyl)-ethanolamine (a) A solution of 3,4,5-trimethoxybenzaldehyde (3.5 g) and methylaminoethanol (1.5 ml), in toluene (50 ml)

was heated under reflux and the water formed during the reaction was distilled azeotropically.

Then the solvent was evaporated under reduced pressure, the residue was dissolved in ethanol and NaBH$_4$ (680 mg) was added to the solution.

After 1 hour at room temperature, the reaction mixture was evaporated to dryness, the residue was dissolved in CH$_2$Cl$_2$ and washed with a diluted solution of KNCO$_3$.

The organic layer was dried on Na$_2$SO$_4$ and evaporated obtaining N-methyl-N-(3,4,5-trimethoxybenzyl)-ethanolamine as a chromatographically pure oil (thin layer chromatography on silica gel, eluent: CH$_2$Cl$_2$:CH$_3$OH:NH$_4$OH =94.5:50.5, detection: U.V. light or I$_2$ vapours).

$^1$H-NMR (60 MHz, CKCl$_3$, TMS)

delta (ppm): 2.2 (3H, s); 2.6 (3H, t); 3.6 (2H, s); 3.8 (2H, t); 4.0 (9H, s); 6.7 (2H, s).

(b) To a solution of 3,4,5-trimethoxybenzaldehyde (100 g) in ethanol 95% (200 ml), methylaminoethanol (43 ml) and Pd on carbon at 5% (10 g) were added. The suspension was hydrogenated at 50° C. and at 3.5 atmospheres H$_2$.

After the theoric absorption of hydrogen, the catalyst was filtered off, the solvent was evaporated under reduced pressure and the residue was distilled obtaining N-methyl-N-(3,4,5-trimethoxybenzyl)-ethanolamine (b.p. 170° C./0.5 mmHg) as a chromatographically pure oil (thin layer chromatography on silica gel, eluent: CH$_2$Cl$_2$:CH$_3$OH:NH$_4$OH =86:10:0.6, detection: U.V. light or I$_2$ vapours).

EXAMPLE 5

Preparation of N,N'-dimethyl-N-(3,4,5-trimethoxybenzyl)-ethylenediamine dihydrochloride (a) By working as described in example 2, but substituting N,N'-diemthyl-N-benzyl-N'-(3,4,5-trimethoxybenzoyl)-ethylenediamine with an equivalent amount of N,N'-dimethyl-N-benzyl-N'-(3,4,5-trimethoxybenzyl)-ethylenediamine obtained as described in example 3, N,N'-dimethyl-N-(3,4,5-trimethoxybenzyl)-ethylenediamine dihydrochloride was obtained (m.p. =183°-158° C. from ethanol/acetone).

(b) By working as described in example 3, but substituting N,N'-dimethyl-N-benzyl-N'-(3,4,5-trimethoxybenzoyl)-ethylenediamine with an equivalent amount of N,N'-dimethyl-N-(3,4,5-trimethoxybenzoyl)-ethylenediamine hydrochloride obtained as described in example 2, N,N'-dimethyl-N-(3,4,5-trimethoxybenzoyl)-ethylenediamine dihydrochloride was obtained.

(c) To a solution of N-methyl-N-(3,4,5-trimethoxybenzoyl)-ethylenediamine (3 g), obtained as described in example 4, in CH$_2$Cl$_2$ (30 ml), SOCl$_2$ (1.282 ml) was added at 5°-10° C. After 2 hours under reflux, the reaction mixture was evaporated under reduced pressure; the so obtained crude of N-(2-chloroethyl)-N-(3,4,5-trimethoxybenzoyl)-methylamine hydrochloride was used for the next step without purification.

After dissolution in absolute ethanol (20 ml), a solution at 25% of methylamine (30 ml) in toluene was added. After 7 hours at 50° C., the reaction mixture was evaporated under reduced pressure. The residue was dissolved in CH$_2$Cl$_2$, washed with H$_2$O, diluted NaOH, the organic layer was dried on Na$_2$SO$_4$ and evaporated under reduced pressure.

The residue was dissolved in ethanol and acidified with ethanol saturated by hydrochloric acid; by dilution with acetone N,N'-dimethyl-N-(3,4,5-trimethoxybenzoyl)-ethylenediamine dihydrochloride was separated.

(d) A solution of 3,4,5-trimethoxybenzaldehyde (150 g) in toluene (300 ml) and N,N'-dimethylethylenediamine (81 ml) was kept under reflux for 2 hours.

Then the solvent was evaporated and Pd on carbon at 10% (30 g) was added to the residue dissolved in ethanol saturated by HCl (215 ml); the suspension was hydrogenated under 3-4 atm pressre.

After absorption of the theoric amount of hydrogen, the solution was worked up as described in example 3; N,N'-dimethyl-N-(3,4,5-trimethoxybenzoyl)-ethylenediamine dihydrochloride was so obtained.

EXAMPLE 6

Preparation of N,N'-dimethyl-N-(3,4,5-trimethoxybenzoyl)-N'-[3,3-di-(4-flurophenyl)-propionyl]-ethylenediamine To a solutin of N,N'-dimethyl-N-(3,4,5-trimethoxybenzoyl)-ethylenediamine (350 g), obtained as described in example 2, in pyridine (4 ), 3,3-di-(4-fluorophenyl)-propionyl chloride (317 g) was added.

After 2 hours the reaction mixture was evaporated under reduced pressure, the residue was dissolved in CH$_2$Cl$_2$ and washed with K$_2$CO$_3$1N. The organic layer was dried on Na$_2$SO$_4$ and evaporated to dryness obtaining N,N'-dimethyl-N-(3,4,5-trimethoxybenzoyl)-N'-[3,3-di-(4-fluorophenyl)-propionyl]-ethylenediamine as a chromatographically pure oil (thin layer chromatography on silica gel, eluent: CH$_2$Cl$_2$:CH$_3$OH:NH$_4$OH =86:10:0.6, detection: U.V. light or I$_2$ vapours).

$^1$H-NMR (60 MHz, CDCl$_3$, TMS)

delta (ppm): 3.1 (6H, s); 3.9 (3H, s); 3.92 (6H, m); 6.65 (2H, s); 7–7.4 (8H, m).

Mass spectroscopy: (M+/e) 527 (100).

EXAMPLE 7

Preparation of N,N'-dimethyl-N-(3,4,5-trimethoxybenzoyl)-N'[3,3-di-(4-fluorophenyl)-propenoyl]-ethylenediamine By working as described in example 1, but substituting N,N'-dimethyl-N-benzyl-ethylenediamine and 3,4,5-trimethoxybenzoyl chloride with an equivalent amount of N,N'-dimethyl-N-(3,4,5-trimethoxybenzoyl)-ethylenediamine obtained as described in example 5 and of 3,3-di-(4-fluorophenyl)-propenoyl chloride respectively and prolonged the reaction time till 24 hours, N,N'dimethyl-N-(3,4,5-trimethoxybenzoyl)-N'-[3,3-di-(4fluorophenyl)-propenoyl]-ethylenediamine was obtained as a chromatographically pure oil (thin layer chromatography on silica gel, eluent: CH$_2$Cl$_2$:CH$_3$OH:-H$_2$O: CH$_3$COOH =79:15:1:1, detection: U.V. light or I$_2$ vapours).

$^1$H-NMR (60 MHz, CDCl$_3$, TMS)

delta (ppm): 2.4 (4H, m); 2.8 (3H, s); 2.9 (3H, s); 3.4(2H, s); 3.8 (9H, s); 6.3 (1H, s); 6.6 (2H, s); 7 (10H, m).

IR spectroscopy (neat): meaningful bands at 1600–1630 cm$^{-1}$.

EXAMPLE 8

Preparation of N,N'-diemthyl-N-(3,4,5-trimethoxybenzyl)-N'-[3,3-di-(4-fluorophenyl)-propionyl]-ethylenediamine hydrochloride By working as described in example 6, but substituting N,N'dimethyl-N-(3,4,5-trimethoxybenzoyl)- ethylenediamine with an equivalent amount of N,N'-dimethyl-N-(3,4,5-trimethoxybenzyl)-ethylenediamine obtianed as described in example 5, N,N'-dimethyl-N-(3,4,5-trimethoxybenzyl)-N'-[3,3-di-(4-fluorophenyl)-propionyl]-ethylenediamine hydrochloride ws obtained (m.p. =86°-88° C. from diisopropylether).

EXAMPLE 9

Preparation of N,N'-dimethyl-N-(3,4,5-trimethoxybenzyl)-N'-[3,3-di-(4-fluorophenyl)-propyl]-ethylenediamine dihydrochloried (Compound II)

(a) By working as descibed in example 3, but substituting N,N'-dimethyl-N-benzyl-N'-(3,4,5-trimethoxybenzoyl)-ethylenediamine with an equivalent amount of N,N'-dimethyl-N-(3,4,5-trimethoxybenzoyl)-N'-[3,3-di-(4-fluorophenyl)-propionyl]-ethylenediamine, obtained as described in example 6, and by using a double amount of LiAlH4, N,N'-dimethyl-N-(3,4,5-trimethoxybenzyl)-N'-[3,3,-di-(4-fluorophenyl)-propyl]-ethylenediamine dihydrochloride was obtained (m.p. =213°-215° C. from absolute ethanol).

¹H-NMR (60 MHz, CDCl₃, TMS)
delta (ppm): 2.4 (3H, s); 2.6 (3H, s); 3 (2H, m); 3.65 (3H, s); 3.68 (6H, s); 6.7 (2H, s); 7.3 (8H, m).

(b) To a solution of N,N'-dimethyl-N-(3,4,5-trimethoxybenzyl)-N'-[3,3-di-(4-fluorophenyl)-propionyl]-ethylenediamine (33.5 g), obtained as described in example 8, in tetrahydrofuran (200 ml), NaBH₄ (7.4 g) was added. The solution was cooled at 5°-7° C. and borotrifluoride etherate (32.8 ml) was added dropwise keeping at that temperature.

After 2 hours at 40° C. the reaction mixture was cooled and HCl 6N (70 ml) was added. After heating at the boiling temperature for 2 hours, the solvent was evaporated under reduced pressure, the residue was dissolved in diluted ammonia and the product was extracted with CH₂Cl₂.

The collected organic layers were dried on Na₂SO₄, filtered and evaporated. The residue was dissolved in ethanol and the solution was acidified with ethanol saturated by HCl; by cooling N,N'-dimethyl-N-(3,4,5-trimethoxybenzyl)-N'-[3,3-di-(4-fluorophenyl)-propyl]-ethylenediamine dihydrochloride was separated (m.p. =213°-215° C. from absolute ethanol).

(c) By working as described in point 9 b), but substituting N,N'-dimethyl-N-(3,4,5-trimethoxybenzyl)-N'-[3,3-di-(4-fluorophenyl)-propionyl]-ethylenediamine with an equivalent amount of N,N'-dimethyl-N-(3,4,5-trimethoxybenzyl)-N'-[3,3-di-(4-fluorophenyl)-propenoyl]-ethylenediamine obtained as described in example 7 and by using a double amount of borontrifluoride etherate, N,N'-dimethyl-N-(3,4,5-trimethoxybenzyl)-N'-[3,3-di-(4-fluorophenyl)-propyl]-ethylenediamine dihydrochloride was obtained (m.p. =213°-215° C. from absolute ethanol).

Pharmacological examples

The following compounds of formula I described in European Patent No. 41,757 were tested in comparison with compound II.

Compound A—N,N'-dimethyl-N-(3,4,5-trimethoxybenyl)-N'-(3,3-diphenyl-propyl)-ethylenediamine

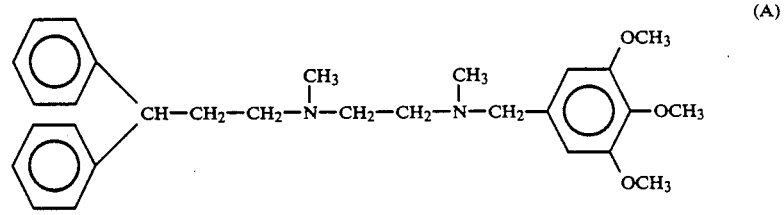
(A)

Compound B—N,N'-dimethyl-N-benzyl-N'-[3,3-di-(4-methoxyphenyl)-3-hydroxy-propyl]-ethylenediamine

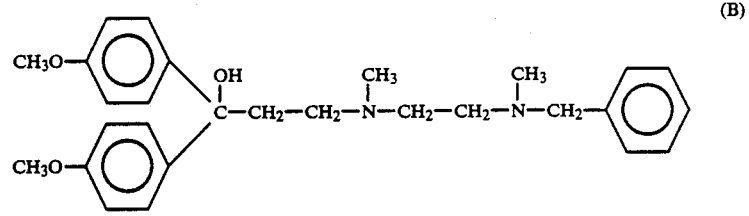
(B)

Compound C—N,N'-dimethyl-N-benzyl-N'-(3,3-diphenyl-propyl)-ethylenediamine

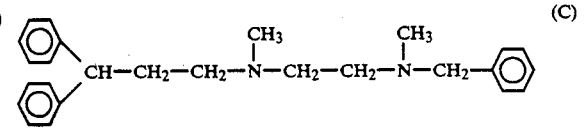
(C)

Compound D—N,N'-dimethyl-N-benzyl-N'(3,3-diphenylallyl)-ethylenediamine

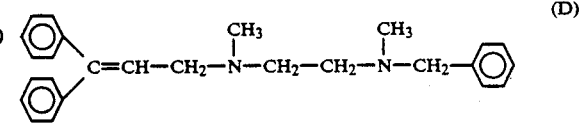
(D)

According to the data reported in European Patent No. 41,757, the most active compound as far as the effects in anti-spasmodic activity is concerned, is Compound A.

EXAMPLE 10

Evaluation of the effects on systemic and coronary hemodynamics

Catheters for detection of arterial pressure and flow electromagnetic transducers for measuring heart flow (heart index) and coronary flow were inserted in dogs anaesthetized with pentobarbital. The resistances were calculated from the pressure/flow ratio. Compound II, as dihydrochloride, and Compound A were administered by intravenous bolus at 0.25 mg/Kg dose.

Effects on systemic hemodynamics, between brackets ( ) the basal value (average values ± standard deviation).

Compound II

Heart rate (beats/min): 156±12 (167±15)
Arterial pressure (mmHg):
 maximum: 130±6* (149±11)
 medium: 89±3** (117±7)
 minimum: 72±2** (101±5)
Maximum ejection rate (ml/sec/m$^2$):
 174.77±10.27*
 (126.79±14.41)
Systolic index (ml/beats/m$^2$): 13.39±1.00* (9.51±1.24)
Heart index (l/min/m$^2$): 2.088±0.240 (1.547±0.147)
Total peripheral resistances (mmHg/l/min.):
 44.366±4.200**
 (78.497±8.587).

Compound A

Heart rate (beats/min): 147±8 (178±11)
Arterial pressure (mmHg):
 maximum: 98 (143±14)
 medium: 71±8 (112±12)
 minimum: 50±3 (97±11)
Maximum ejection rate (ml/sec/m$^2$):
 135.58±17.55
 (138.59±21.74)
Systolic index (ml/beatsm$^2$): 11.11±1.49* (10.09±1.29)
Heart index (l/min/m$^2$): 1.615±0.237 (1.820±0.311)
Total peripheral resistances (mmHg/l/min.):
 45.023±2.849
 (63.985±5.037).

Compound A showed borderline effects on peripheral vascular resistances and on arterial pressure.

Comparable effects to compound II were observed only after the administration of a dose of Compound A four times higher (i.e. 1 mg/kg) but, differing from Compound II, at this dose Compound A induced a decrease in cardiac output.

Effects on coronary hemodynamics, between brackets ( ) the basal value (average values ± standard deviation), of Compound II
Heart rate (beats/min): 143±15 (±14)
Arterial pressure (mmHg):
 maximum: 142±5 (145±3)
 medium: 102±5 (116±4)
 minimum: 87±3 (103±6)
Left circumflex coronary artery flow (ml/min)
 101.6±10.8*
 (41.3±3.7)
Average coronary resistances (mmHg/ml/min)
 1.301±0.141*
 (2.887±0.381)

(* p<0.05, ** p<0.01 Student t for couple of data).

EXAMPLE 11

Evaluation of specific antagonistic activity to serotonin (5TH) effects (a) Antagonism towards vascular spasms induced by serotonin. Vascular strips of mesenteric artery and rabbit aorta were put into baths for isolated organ containing Krebs solutions at 37° C. and aerated with a mixture of oxygen and carbon dioxide 95:5.

The addition of serotonin to the bath causes a spasm which is detected by a strength transducer.

The antagonistic activity of compound II, evaluated as inhibiting concentration (IC$_{50}$), gave the following results:

Mesenteric artery: IC$_{50}$=0.22 μM (fiduciary limits 0.15–0.31)
Aorta: IC$_{50}$=0.16 μM (finduciary limits 0.05–0.56).

At the same concentration, the tested compounds of formula I showed to be substantially inactive.

(b) Enhancement in aggregation induced by serotonin.

The addition of 5HT to dog blood platelets causes the aggregation of non-aggregating concentrations of adenosine diphosphate, collagen and adrenaline.

The effects of compound II (dihydrochloride) expressed as single concentration, were evaluated by pre-incubating the blood platelets with different concentrations of the product and expressed as Threshold Inhibiting Concentration (TIC):

Adenosine diphosphate TIC=37±20 μM
Collagen TIC=5.6±4 μM
Adrenaline TIC=11±5.4 μM (c) Change of the shape of blood platelets induced by serotonin. The addition of serontonin to rat blood platelets causes a change in the shape which is measured by an aggregometer as maximum decrease in light transmission.

Compund II (dihydrochloride) was tested by pre-treating the blood platelets with different concentrations of product and the activity was expressed as 50% inhibiting concentration (IC$_{50}$).

IC$_{50}$ of compound II resulted to be 8.35±1.35 μM.

EXAMPLE 12

(a) Evaluation of the activity in the prevention of the formation of arteriosclerotic plaques Rabbits HY/CR were fed with iperchloesterolemic diet (2% (cholesterol) for 60 days at the end of which, by planimetry after colouring aorta with Sindon Black, the extent of arteriosclerotic plaques was evaluated.

Compund II (dihydrochloride) administered by subcutaneous route at 3 mg/Kg dose 2 times a dya for 60 days reduced meaningfully (60%) the formation of plaques.

(b) Evaluation of the activity in inhibiting arterial smooth cell proliferation A culture of smooth muscle cells was isolated by rat aorta incubated in the presence of the tested Compounds II, A, B, C and D for 24, 48 and 72 hours in a minimal essential medium added with bovine fetal serum: at the above intervals the number of cells in the culture was counted by a hemocytometer and compared with the number of cells in a control culture. Compound II inhibited meaningfully cell proliferation at a concentration of 5 μM and it showed a IC$_{50}$ value of 10 μM.

At these concentrations the tested compounds of formula I did not show any antiproliferative effect.

EXAMPLE 13

Preparation of injectable pharmaceutical compositions

Composition of a single vial
Compound II (dihydrochloride): 5 mg
Sodium chloride: 12 mg
Water for injectable preparations q.s. up to: 2 ml
Preparation of vials
Bis-distilled water (50 l) was poured into a dissolver with heating jacket and compound II (dihydrochloride) (268.75 g) was added under stirring. The mixture was gently heated (50° C.) till complete dissolution.

A solution of sodium chloride (860 g) in bis-distilled water (5 l) was, then, pooured into the dissolver and the further necessary water was added up to volume (107.5 l).

The stirring was kept on, at room temperature, till homogeneous solution.

The solution was filtered through a filtering membrane and put into vials under nitrogen (2 ml a vial).

The vials were put in autoclave and sterilized at 121° C. for 20 minutes.

About 50.000 vials containing an injectable solution of compound II at the dose of 5 mg/vial were so obtained.

EXAMPLE 14

Preparation of pharmaceutical compositions in tablets

Compound II (dihydrochloride) (2 kg), starch (2 kg), microcrystalline cellulose (2.5 kg), talc (1.4 kg) and magnesium stearate (0.1 kg) were passed through a vibrating screen with net 36 mesh/cm$^2$.

The ingredients were, then, mixed by a blade mixer till an exact distribution and the mixture was dry-pressed by a rotative compressed tablet machine.

40.000 tablets weighing 200 mg with a dose of 50 mg of compound II (dihydrochloride) were so obtained.

What we claim is

1. The comound N,N'-dimethyl-N-(3,4,5-trimethoxybenzyl)-N'-[3,3-di-(4-fluorophenyl)-propyl]-ethylenediamine of formula

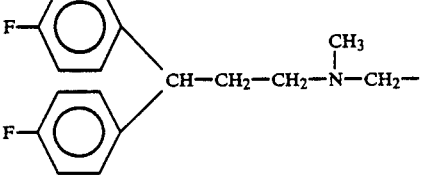

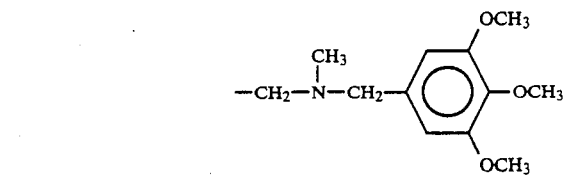

(II)

and its salts with pharmaceutically acceptable acids.

2. A method for the treatment of cardiac decompensation consisting in administering to the patient an effective amount of a compound according to claim 1.

3. A method for the treatment of coronary diseases consisting in administering to the patient an effective amount of a compound according to claim 1.

4. A method for the preventive or curative treatment of arteriosclerosis consisting in administering to the patient and effective amount of a compound according to claim 1.

5. A pharmaceutical composition containing an effective amount of a compound according to claim 1 and a pharmaceutically acceptable carrier.

* * * * *